(12) United States Patent
Benecke et al.

(10) Patent No.: US 9,290,698 B2
(45) Date of Patent: Mar. 22, 2016

(54) BIOBASED POLYOLS FOR POTENTIAL USE AS FLAME RETARDANTS IN POLYURETHANE AND POLYESTER APPLICATIONS

(75) Inventors: Herman P. Benecke, Columbus, OH (US); Daniel B. Garbark, Blacklick, OH (US)

(73) Assignee: Battelle Memorial Institute, Columbus, OH (US)

(\*) Notice: Subject to any disclaimer, the term of this patent is extended or adjusted under 35 U.S.C. 154(b) by 151 days.

(21) Appl. No.: 13/810,215

(22) PCT Filed: Jul. 15, 2011

(86) PCT No.: PCT/US2011/044131
§ 371 (c)(1),
(2), (4) Date: Jan. 15, 2013

(87) PCT Pub. No.: WO2012/009609
PCT Pub. Date: Jan. 19, 2012

(65) Prior Publication Data
US 2013/0150475 A1    Jun. 13, 2013

Related U.S. Application Data

(60) Provisional application No. 61/364,557, filed on Jul. 15, 2010.

(51) Int. Cl.
| C07D 307/46 | (2006.01) |
| C09K 21/06 | (2006.01) |
| C07D 307/68 | (2006.01) |
| C09K 21/10 | (2006.01) |

(52) U.S. Cl.
CPC ............. *C09K 21/06* (2013.01); *C07D 307/46* (2013.01); *C07D 307/68* (2013.01); *C09K 21/10* (2013.01)

(58) Field of Classification Search
CPC ................................................. C07D 307/46
See application file for complete search history.

(56) References Cited

U.S. PATENT DOCUMENTS

| | | | |
|---|---|---|---|
| 3,238,161 A * | 3/1966 | Wicker et al. | 528/295.5 |
| 3,865,757 A | 2/1975 | Wade | |
| 4,029,611 A | 6/1977 | Cenker et al. | |
| 4,170,584 A * | 10/1979 | Heckles | 524/104 |
| 4,318,999 A | 3/1982 | Dunlop et al. | |
| 4,973,715 A * | 11/1990 | Roux et al. | 549/502 |
| 6,750,210 B2 | 6/2004 | Biggadike et al. | |
| 6,759,398 B2 | 7/2004 | Biggadike | |
| 6,777,399 B2 | 8/2004 | Biggadike et al. | |
| 6,777,400 B2 | 8/2004 | Biggadike et al. | |
| 6,858,593 B2 | 2/2005 | Biggadike et al. | |
| 6,858,596 B2 | 2/2005 | Biggadike et al. | |
| 7,101,866 B2 | 9/2006 | Biggadike et al. | |
| 7,125,985 B2 | 10/2006 | Biggadike et al. | |
| 7,132,532 B2 | 11/2006 | Biggadike et al. | |
| 7,144,845 B2 | 12/2006 | Biggadike et al. | |
| 7,541,350 B2 | 6/2009 | Biggadike et al. | |
| 2002/0165211 A1 | 11/2002 | Biggadike et al. | |
| 2002/0173496 A1 | 11/2002 | Biggadike et al. | |
| 2002/0177581 A1 | 11/2002 | Biggadike | |
| 2003/0109511 A1 | 6/2003 | Biggadike et al. | |
| 2003/0144257 A1 | 7/2003 | Biggadike et al. | |
| 2003/0153542 A1 | 8/2003 | Biggadike et al. | |
| 2003/0199485 A1 | 10/2003 | Biggadike et al. | |
| 2004/0220156 A1 | 11/2004 | Biggadike et al. | |
| 2004/0220157 A1 | 11/2004 | Biggadike et al. | |
| 2004/0220162 A1 | 11/2004 | Biggadike et al. | |
| 2004/0224931 A1 | 11/2004 | Biggadike et al. | |
| 2004/0224932 A1 | 11/2004 | Biggadike et al. | |
| 2004/0224934 A1 | 11/2004 | Biggadike et al. | |
| 2004/0225139 A1 | 11/2004 | Biggadike et al. | |
| 2005/0020549 A1 | 1/2005 | Biggadike et al. | |
| 2005/0043284 A1 | 2/2005 | Biggadike et al. | |
| 2005/0152845 A1 | 7/2005 | Biggadike et al. | |
| 2005/0164996 A1 | 7/2005 | Biggadike et al. | |
| 2005/0164997 A1 | 7/2005 | Biggadike | |
| 2006/0002861 A1 | 1/2006 | Biggadike | |
| 2007/0027128 A1 | 2/2007 | Biggadike et al. | |
| 2008/0182944 A1 | 7/2008 | Benecke et al. | |
| 2009/0156567 A1 | 6/2009 | Biggadike | |
| 2011/0124839 A1 | 5/2011 | Matsuda et al. | |

FOREIGN PATENT DOCUMENTS

| EP | 1775305 | 4/2007 |
| SI | 1305329 | 4/2008 |
| WO | 2004024745 | 3/2004 |

OTHER PUBLICATIONS

Saber, H.H. et al.; Numerical and Experimental Investigations of Fire Behavior Due to Polyurethane Foam and Wood Cribs in a Medium-Sized Residential Room; Research Report #RR-291; Mar. 8, 2010; 84 pages; Institute for Research in Construction Fire Research Program, National Research Council Canada.

\* cited by examiner

*Primary Examiner* — Michael L Leonard
(74) *Attorney, Agent, or Firm* — Yimei C. Hammond; Kremblas & Foster

(57) ABSTRACT

The invention provides for new flame retardant non-furan dicarboxylic acid (FDCA) based polyols; oligomers and polymers made from these new polyols with flame retardation properties; and methods of using them as a part or all of the flame retardation composition/material, such as foams and binders.

5 Claims, No Drawings

BIOBASED POLYOLS FOR POTENTIAL USE AS FLAME RETARDANTS IN POLYURETHANE AND POLYESTER APPLICATIONS

FIELD OF THE INVENTION

The invention provides for non-furan dicarboxylic acid based flame retardant polyols, and the use of these polyols in polyurethane and/or polyester applications.

BACKGROUND OF THE INVENTION

Polyols are materials used in a wide variety of applications, such as flame retardancy, cross-linkers, chain extender, chain terminators, and/or polyurethane synthesis. U.S. patent application publication 2008/0182944 (Benecke et al.) describes a series of new polyols used in formaldehyde free binders in fiberglass applications. Benecke et al. disclose that the new polyols are based on furan dicarboxylic acid (FDCA), and these polyols are disclosed to be useful as a binder. However, the current pricing of FDCA is too high for industrial use. Until FDCA is more cost effective, alternative polyols are needed.

Furan-containing polyols, compounds or materials ("furan compounds") are known for their char formation when heated to high temperatures, and as such, they are regarded as possibly having some flame-retardant properties when combined with other known flame-retardants, cf. U.S. Pat. Nos. 4,029,611; 3,865,757; 4,318,999, and U.S. patent application publication no. US 2011/0124839. The other known flame-retardants are considered to be main contributor to the flame retardation properties of the foam; while the furan compounds were used along with other catalysts for promoting carbodiimide linkage so that the resulting foams could have better processability without losing any flame retardant properties (U.S. Pat. No. 4,029,611). These other commonly used flame retardants are phosphorus-containing inorganic compounds (U.S. Pat. No. 3,865,757), tris(2-chloroethyl) phosphate (U.S. Pat. No. 4,029,611), halogenated compound (U.S. Pat. No. 4,318,999), phosphorus element (U.S. patent application publication no. US 2011/0124839).

In other words, the flame retardation properties of the furan resins were not studied independent of the presence of other known flame retardants, the inclusion of which can increase the expense of the foam products and causing changes to the foam characteristics of the product. It is well known that cell structure of the foam and crosslinked polymers can affect the flame retardancy, such as the burning rate of the foam. According to Saber et al. in a 2010 report # RR291 to the National Research Council Canada, crosslinking bond strength of the flame retardant materials is important in flame retardation (the report is entitled "Numerical and Experimental Investigations of Fire Behavior of Polyurethane Foam and Wood Cribs in a Medium-Sized Residential Room"). The foam is a cross-linked polymer, and at an elevated temperature, the melting cannot occur until these crosslinks are broken. The crosslinks take several forms and the proportions depend on the particular foam formulation.

The bond strength of a furan compound is dependent its structure, or dependent on the addition of another flame retardant element, such as phosphorus. For example, Matsuda et al. disclose in U.S. patent application publication no. US 2011/0124839 that polyethylene 2, 5-furan dicarboxylate has been unable to achieve high flame retardancy such as V-0 or V-1 in UL94 Standard by itself. However, Matsuda et al. states that a polyester copolymer, which was formed by adding a furan diol or an aliphatic diol, and 9,10-dihydro-9-oxa-10-phosphaphenanthrene-10-oxide to polyethylene-2,5-furan dicarboxylate (DOPO), had a increased flame retardant properties so that the burning test result for the copolymer corresponds to V-0 in UL94 Standard. As such, they conclude that "when the content of the phosphorus atom is from 0.3% by weight to 1.5% by weight," the resulting furan copolymer shows a good flame retardancy (the burn test corresponds to V-O).

Therefore, the addition of other known flame retardants can affect the cell structure of the foam, and may provide additional crosslinked bonds that can also interact and/or crosslink with the furan resins/compounds. As such, the furan compounds might not contribute significantly, or if any, flame retardant properties to the resulting foam, especially at a low furan content, such as 4 wt % or lower.

In addition, these known furan compounds are commonly condensation products of furfuryl alcohol with formaldehyde in an acidic environment. At high temperatures, the foams with such furan resins will likely release formaldehyde, which can cause significant negative health effects because formaldehyde is a known toxic substance. There is increasing demand for phasing out the halogenated flame retardants (FR) because of high and toxic smoke generation.

A furan ring-containing polyol, 2-furoyldiethanolamide, is disclosed in U.S. Pat. Nos. 7,541,350; 7,144,845; 7,132,532; and U.S. patent application publication no. US 2009/015657. The patents and the patent application do not suggest or teach that the polyol might have flame retardant properties, nor are the patents and the patent application interested in the flame retardant property of the polyol or the typical uses of polyols as precursors for polyurethanes or polyesters. The polyol is described as a more water-soluble by-product of a formulation containing anti-inflammatory androstane derivative. The polyol's improved water solubility enabled the polyol to be removed by water washing, thereby providing an improved process for synthesis of a specific drug.

BRIEF DESCRIPTION OF THE INVENTION

There exists a need for non-FDCA based furan polyols that can provide flame retardant properties in polyurethane and polyester applications, such as foams and binders, without any other flame retardants or additives. These other flame retardants or additives can also be referred to as flame retardant compounds, material, ingredient, or element.

Broadly, the invention provides for biobased polyols that have flame retardation properties. In other words, the present invention includes a flame retardant polyol that comprises any of five polyols illustrated by the following five formulae, including their derivatives illustrated by substituents on the furan ring and/or nitrogen containing arms

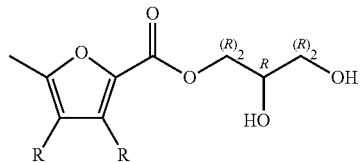

Polyol 1

Polyol 2

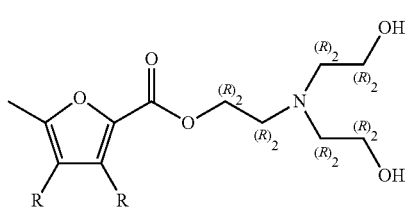

Polyol 3

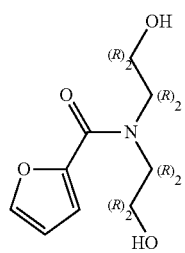

Polyol 4

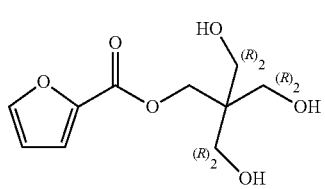

Polyol 5

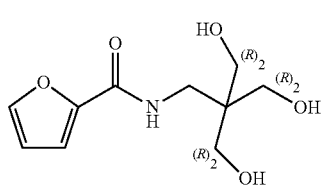

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

Further, the present invention includes a method of using any of the five polyols and/or their derivatives as one or more flame retardant components in polyurethane and polyester applications.

A first flame retardant polyol having the formula of Polyol 1, is disclosed

Polyol 1

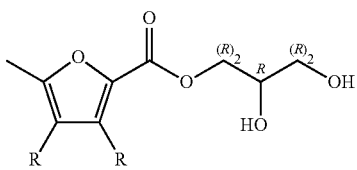

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

A second flame retardant polyol having the formula of Polyol 2, is disclosed

Polyol 2

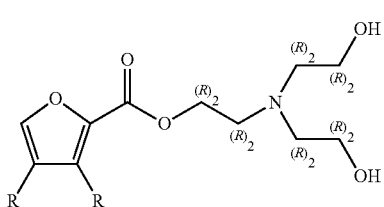

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

A method of using a third polyol as a flame retardant, wherein the polyol has a formula of Polyol 3, is disclosed Polyol 3

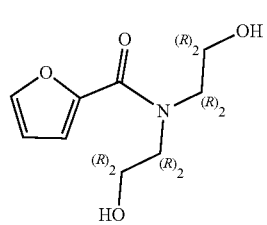

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

A fourth flame retardant polyol is presented by:

Polyol 4

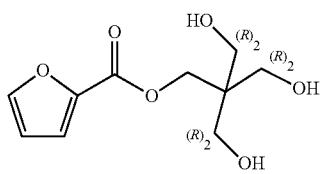

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

A fifth flame retardant polyol is represented by:

Polyol 5

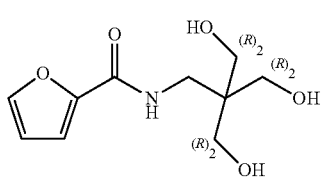

wherein each R is the same or different, each (R)$_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

According to some embodiments, the present invention provides for a mixture of polyols, which include two or more polyols selected from the group consisting of

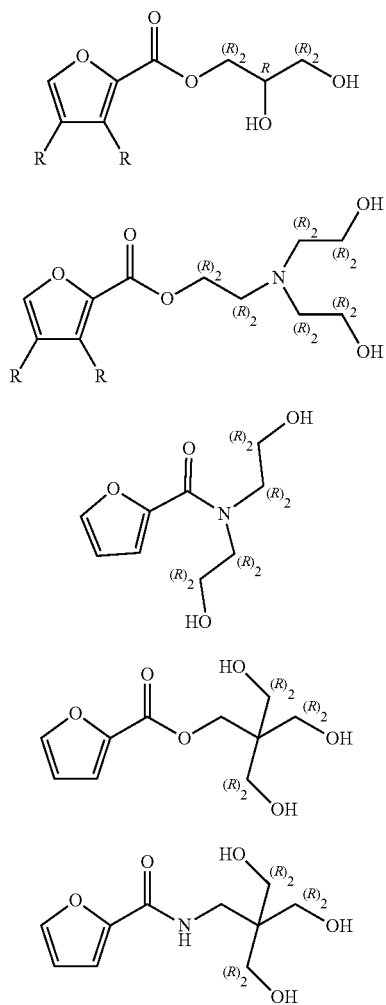

One or more Polyols 1 to 5 and/or a mixture thereof are typically reacted to form oligomers that can be further polymerized into flame retardant foams and/or binders. Such an oligomer includes a reaction product of a polyol selected from the group consisting of Polyol 1, Polyol 2, Polyol 3, Polyol 4, and Polyol 5, and a polyfunctional acid or a polyfunctional nitrile. Alternatively, the oligomer is the reaction product of mixtures of two or more polyols selected from Polyol 1 through Polyol 5, and a polyfunctional acid or a polyfunctional nitrile; wherein the oligomer has one or more hydroxyl terminals.

According to some other embodiments, the present invention provides for a flame retardant foam article obtained by incorporating one or more Polyols 1 to 5, polyol mixtures, and/or oligomers as described above. Preferably, the polyols, polyol mixtures and/or oligomers of the present invention (as described above) are present in the amount of about 0.25% to about 78%.

According to some other embodiments, the present invention provides for a flame retardant binder obtained by incorporating one or more flame retardant Polyols 1 to 5, polymer mixtures, and/or oligomers as described above.

DETAILED DESCRIPTION OF THE INVENTION AND BEST MODE

Broadly, the present invention provides for one or more biobased polyols that have flame retardation properties, especially in polyurethane and polyester applications, such as foams and binders. These polyols can provide flame retardant properties without the presence of any other flame retardants or additives, reducing costs of producing the foams and/or binders, and possibly making the production process more manageable. These other flame retardants or additives can also be referred to as flame retardant compounds, material, ingredient, or element. The percentage and/or "%" mentioned in this application refers to a percentage based on weight or as "wt %."

These polyols might be any one or more of polyols derived from furanic acids, other than furan dicarboxylic acid. All of these polyols have one or more hydroxy terminals, preferably having two to three hydroxy terminals. Furanic acids suitable for the present invention include, but are not limited to, 2-furoic acid, 3-furoic acid, 3-methyl-2-furoic acid, hydroxylated furan mono-carboxylic acids, and a mixture thereof. 2-furoic acid is a mono-acid with a furan ring, and it is approximately 4% soluble in water.

One embodiment of the present invention is one or more polyols having Formulae 1 and/or 2 (also referred to as "Polyol 1" and "Polyol 2"), both of which have two hydroxyl groups (also called "diols"). These two polyols are ester derivatives of 2-furoic acid:

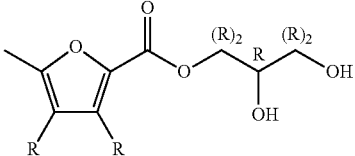

Formula 1

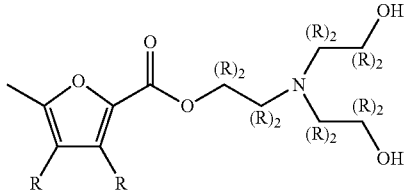

Formula 2 wherein each R is the same or different, each $(R)_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

Other embodiments of the present invention provide for amide derivatives of 2-furoic acid, which have a Formula 3 (also referred to as "Polyol 3") as shown below:

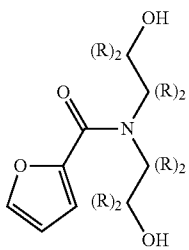

Formula 3 wherein each R is the same or different, each $(R)_2$ represents two radicals R that are the same or different, R can be hydrogen, alkyl of 1-12 carbon atoms, halogen, halogenalkyl, salt, aryl, cycloalkyl, heteroaromatic, amine, carboxy, carboalkoxy, vinyl, substituted vinyl, ether, alkyl ether, alkene, alkyne, aldehyde, carbonate, ester, or carboxamide.

The more specific examples of Polyol 1 and Polyol 3 include, but are not limited to, 2-furoic mono-glyceride (Polyol 1-A) and 2-furoic diethanolamide (Polyol 3-A), respectively, which have the following structures:

Polyol 1-A

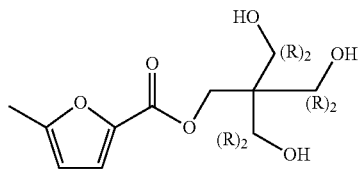

2,3-dihydroxypropyl furan-2-carboxylate or glyceryl furoate

Polyol 3-A (Polyol 3-A structure)

2-furoic diethanolamide or IUPAC name N,N-bis(2-hydroxyethyl)furan-2-carboxymide Other embodiments of the present invention provide for one or more polyols having Formulae 4 and/or 5 (also called "Polyol 4" and "Polyol 5"), which are disclosed below:

Formula 4

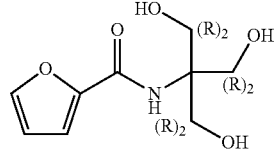

-continued

Formula 5

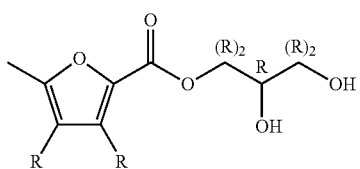

Both Polyols 4 and 5 contain three terminal hydroxyl groups so they are also referred as triols. Triols can be produced by forming an amide with tris(hydroxymethyl)aminomethane or an ester with a tetra-ol such as diglycerine or pentaerythritol.

In some further embodiments of the present invention, all of the above polyols may be provided as any of the polyols selected from Polyols 1 to 5, or a mixture of two or more polyols selected from Polyols 1 to 5:

Polyol 1

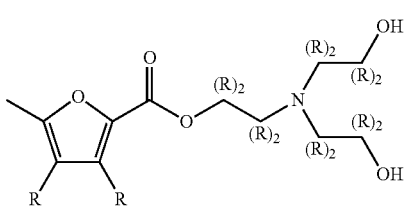

Polyol 2

Polyol 3

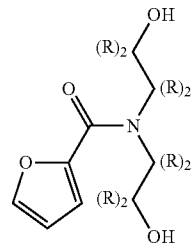

Polyol 4

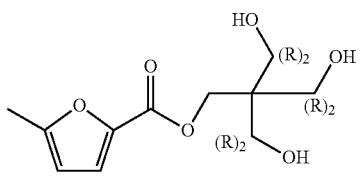

Polyol 5

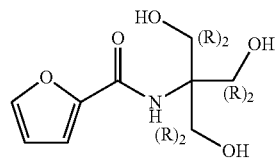

The above Polyols 1 to 5 and mixtures of two of more of these Polyols 1 to 5 (polyol mixtures) are all expected to have flame retardant properties without any other flame retardant material or compound, especially when they are used in polyurethane and polyester applications, such as foams and/or binders. As such, these polyols can be a part or all of the flame retardant material/composition, such as foams or binders.

Further, these polyols are difunctional or multifunctional. That is, these polyols can also be used as chain extenders in polymer applications. In addition, Polyols 4 and 5 are capable of being cross-linker or a binder in polyurethane and polyester applications, typically foams and/or binders, due to their having three hydroxyl groups. As such, while not wishing to be bound by theory, it is presently believed that the inclusion of the polyols of the present invention in foams and/or binders may reduce the amount of the certain ingredients, and/or the number of ingredients, for producing the flame retardant foams and/or binders. Accordingly, the use of the present invention may reduce the cost of producing the foams and/or binders.

One or more Polyols 1 to 5 or a mixture thereof can react with one or more polyfunctional acids to form oligomers, which can be further polymerized into binders or other materials, and which also possess flame retardant properties. In other words, such an oligomer is the reaction product of one or more polyols selected from the group consisting of polyols according to Formula 1, Formula 2, Formula 3, Formula 4, and Formula 5; and a polyfunctional acid or polyfunctional nitrile. All of the above oligomers have one or more hydroxyl-terminals.

An example of the above oligomer and how the oligomer is formed are shown below:

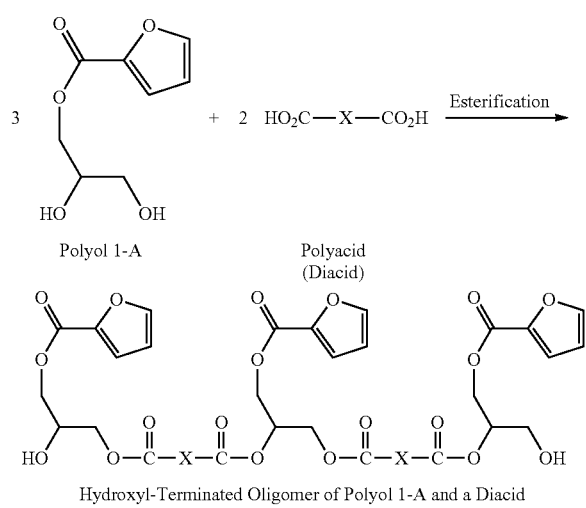

In this example, Polyol 1-A (an example of Polyol 1) reacts with polyacid (a diacid) to form a hydroxyl-terminated oligomer of Polyol 1-A and a polyacid.

In the foregoing Formulae 1 to 5, the number of carbon atoms in the R groups is typically up to about 12. In some embodiments the R group is typically hydrogen, or an alkyl of 1-12 carbon atoms.

According to some embodiments of the present invention, Polyols 1 to 5, polyol mixtures, and the oligomers and/or polymers resulted from incorporating one or more Polyols 1 to 5 can impart flame retardant properties to the resulting foams and/or binders without any other flame retardant compounds or elements. The lack of the need for other flame retardant compounds can result in significant reduction in production cost in terms of raw materials and processing time.

Flame Retardant Foams Using Polyols and/or Oligomers of the Present Invention:

According to some broad alternative embodiments, the present invention provides a flame retardant foam article obtained by incorporating one or more Polyols 1 to 5, polymer mixture, and/or oligomers as described above.

Any one or more Polyols 1 to 5, polymer mixture, and/or oligomers are capable of providing flame retardation to the foam without any other flame retardant additives or elements. As such, the polyols, polyol mixtures and the oligomers of the present invention are able to provide flame retardant properties at a significant reduced cost in terms of raw materials (no other flame retardants) and processing time (adding these other flame retardants. In addition, the elimination of the other flame retardants may make the entire production process more manageable.

Moreover, the polyols and oligomers are capable of providing flame retardation properties to foam even at a very low percent loading, further reducing the production cost of making the foam. For example, a loading of only about 8.3 wt % of 2-furoic tris(hydroxymethyl)aminomethane amide (an example of Polyol 5) was able to reduce the burn rate of the polyurethane rigid foam by almost 25% (as shown by Example 4 below). More importantly, the resulting foam exhibited a similar density to that of the foam without Polyol 5. Please note that 8.3 wt % of 2-furoic tris(hydroxymethyl) aminomethane amide is equivalent to about 4 wt % furan content loading because 2-furoic tris(hydroxymethyl)aminomethane amide has about 48.1 wt % furan content.

Foam is a substance that is formed by trapping many gaseous bubbles in a liquid or solid. As such, there are liquid foams and solid foams. The present invention is typically used in solid foams. Solid foams can be classified into two types based on their pore structure: open cell structured foams (also known as reticulated foams or flexible foams) and closed cell foams (known as rigid foams). Flexible foams can be produced in both high and low densities. Rigid foams are highly cross-linked polymers with a closed cell structure that prevents gas movements. A special class of closed-cell foams is known as syntactic foam, which contains hollow particles embedded in a matrix material. One particular syntactic foam employs shape memory polymer as its matrix, enabling the foam to take on the characteristics of shape memory resins and composite material. Other miscellaneous foams include integral skin foam, which is a type of foam with a high-density skin and a low density core.

Currently, polyurethane is the most commonly used material for foam products, called polyurethane foams. The polyols of the present invention can be used in any polyurethane foam to impart flame retardant properties to the foam. Most polyurethane foams consist of the following components: polyol(s), polyisocyanates or diisocyanates, blowing agent and other additives. Polyols and isocyanates are liquid polymers that, when combined with the blowing agent (typically water), produce an exothermic reaction forming the polyurethane.

In the polyurethane foams of the present invention, polyol(s) refers to the polyol system, including one or more Polyols 1 to 5 and/or the resulting oligomers; and polyisocyanates refer to the isocyanate system. That is, the polyol system of the present invention includes one or more base polyol and one or more new polyols, in which the new polyol includes one or more Polyols 1 to 5, polyol mixtures, and/or oligomers of the present invention. The type and amount of total polyols used will determine whether the foam produced is flexible or rigid.

The "base polyol," which is used in the polyol system in accordance with the present invention, is any of the commercially available conventional polyols used in producing foams other than the polyols and/or oligomers of the present invention. Typical base polyols of the foam are active hydrogen monomers based on polyesters, polyethers, or hydrocarbon materials that contain at least two active hydrogen atoms. Typically, the commercial polyols consist of a polyether based on ethylene and/or propylene oxide. Preferably, the base polyols are biobased polyols. More preferably, they are sucrose/glycerin-based polyols, such as Jeffol SG-360.

While not wishing to be bound by theory, it is presently believed that most of the polyols in the polyol system react immediately with isocyanates in the isocyanate system when added together, and as such, the polymerization and the shaping processes are often combined into one step. During the polymerization process, the polyols in the polyol system (also called the polyol mixture) and polyisocyanate molecules link and interconnect together to form a three dimensional material. It is also believed that the polyols of the present invention are compatible with this polymerization process, and preferably, they enhance the polymerization process.

Thus, accordingly to some embodiments, the polyol system (or the polyol mixture) of the present invention comprises about 5 wt % to about 95 wt % of one or more Polyols 1 to 5, polyol mixtures, and/or oligomers of the present invention. The foam of the present invention comprises 5 wt % to about 80 wt % of the total polyols in the polyol system, preferably in the range of about 30 to about 50 wt %. Preferably, the flame retardant foam contains the polyols, polymer mixtures, and/or oligomers of the present invention in the amount of about 0.25% to about 78%. More preferably, the foam contains about 1.5 wt % to about 48 wt % (based on the total weight of the foam) of one or more new polyols, in which the new polyol includes one or more Polyols 1 to 5, polyol mixtures, and/or oligomers of the present invention.

The isocyanate system of the present invention may be di- or polyisocyanate or a mixture thereof, including polymeric isocyanate (PMDI). The two polyisocyanates most commonly used are diphenylethane diisocyanate (MDI) and toluene diisocyanate (TDI). MDI is generally used in rigid foams, whereas TDI is typically used for flexible foam applications. Blends of MDI and TDI are also used.

A wide range of additives can also be used. Catalysts (tin and amines) speed up the reaction, allowing large volume production runs. Blowing agents are required to produce foam because they form gas bubbles in the polymerizing mixture. Flexible foams are typically made using the carbon dioxide formed during the reaction of water (typical blowing agent) with isocyanate. Rigid foams use hydrochlorofluorocarbons (HCFC5), hydrofluorocarbons (HfCs), and pentanes as the blowing agents.

Surfactants are preferably used for controlling the size of bubbles, and they include silicones, polyethers, and other similar materials. Other additives that may be used include cross-linking agents, chain-extending agents, fillers, flame retardants and coloring materials, depending on the application.

The molecular structure, amount and reaction temperature of each ingredient determine the characteristics and subsequent use of the foam, including flame retardant properties. According to Saber et al. in a 2010 report to the National Research Council Canada, the properties of the polyurethane vary widely due to the composition, nature and proportions of many ingredients. For example, the cure rate is influenced by the functional group reactivity and the number of the functional isocyanate groups. The mechanical properties are influenced by the functionality and molecular shape. The flame retardant properties of the foam are influenced by both mechanical and chemical properties, such as cell shape/structure and crosslinking bond strength. Saber et al. also disclose that as the fire spreads, for any particular segment of the foam (mostly the outer portion first), the first step in the thermal decomposition of the polyurethane foam was the break-up of the urethane-urea blocks leading to collapse of the cellular structure. At the completion of this step, the cellular structure is transformed to a tarry, viscous liquid. In the second step, the more stable polyol segment decomposes.

Therefore, each formulation must be designed with the proper ingredients to achieve the desired properties of the final material. For instance, a switch in blowing agent may require an increase in this additive to maintain thermal properties. The amount of the blowing is one of the major factors in determining the density of the foam. Therefore, increasing the amount of blowing agent requires more water and a possible switch in surfactants in order to maintain optimum bubble size and formation rates during foaming. The stiffness and hardness of polyurethane can also be tailored by changing the level of flexible polyol in the chemical formation. By mixing different combinations of the starting materials, the rates of the reactions and overall curing during processing can be controlled.

Furan compounds are known to be excellent char-formers (U.S. Pat. No. 3,865,757). The char formation is thought to prevent the spreading of fire and/or cellular degradation because the char has enough integrity to stay in place, keeping some heat of the external fire from the rest of the foam (U.S. Pat. No. 4,708,975). However, it is unclear to what extent the char formation can contribute to the flame retardant properties of the foam. As discussed before, some polyols of furan compounds (U.S. patent application publication no. 2011/0124839 by Matsuda et al.) can provide better flame retardancy as a dried polyester copolymer than that of the other furan compounds. However, it is important to note that these furan polyols contain another known flame retardant element, phosphorus. Matsuda et al. state that "when the content of the phosphorus atom is from 0.3% by weight to 1.5% by weight," the resulting furan copolymer shows a good flame retardancy (the burn test corresponds to V-O). Further, Matsuda et al.'s polyols were used to produce a molded polyester co-polymer, so they might not be compatible with other ingredients of the foam so as to produce robust flame retardant foams. As such, it is unclear whether or not a furan polyol alone can improve the flame retardation properties of the foam without any other flame retardant element, or even whether or not the furan polyol can be compatible with other ingredients of the foam so as to produce a usable or robust foams.

For example, as shown in Example 4, 50 wt % loading (based on the total amount of the polyols) of the 2-furoic tri(hydroxymethyl)aminomethane amide (Polyol 5) changed the apparent cell structure and density when compared to that of the referenced foam without Polyol 5. As the result, even though the resulting foam has a slightly higher flame retardation property, its flame retardancy is lower than that of 25% loading of the same Polyol 5. It is possible that the change in cell structure and density can cause a reduction in the flame retardancy when comparing the flame retardancy of 50 wt % to that of 25 wt %. Alternatively, it is also possible that the slight increase in flame retardancy (as compared to the reference foam without Polyol 5) can be caused by the change in cell structure and density. Therefore, the flame retardancies of two different loading percentages (50 wt % versus 25 wt % Battelle Polyol based on the total weight of the polyol system) cannot be compared directly because of the differences in the densities of the resulting foams.

On the other hand, the 25 wt % loading of Polyol 5 (2-furoic tris(hydroxymethyl)aminomethane amide) based on the total weight of the polyol system was able to produce a flame retardant foam (the Polyol 5 foam) with similar density as that of the foam without any Polyol 5 (the reference foam). The Polyol 5 foam incorporated about 8.3 wt % of Polyol 5 based on the total weight, which contained only about 4 wt % furan content. The reference foam contained no additional flame retardant ingredient. The burn rate of the Polyol 5 foam was about 25% lower than that of the reference foam (Example 4).

Therefore, Polyol 5 was shown to impart flame retardancy to the foam at a low furan content of about 4 wt % without the addition of any other flame retardant ingredient or element. It is currently believed that any one or more Polyols 1 to 5, polyol mixtures, and/or oligomers of the present invention are able to impart flame retardancy to the foam at a low furan content without the addition of any other flame retardant ingredient or element Flame Retardant Binders Using One or More Polyols 1 to 5 and/or Oligomers of the Present Invention:

According to some broad alternative embodiments, the present invention provides flame retardant binders obtained by incorporating one or more Polyols 1 to 5, polyol mixture, and/or oligomers as described above. Polyols 1 to 5 of the present invention, and/or polyol mixtures can be reacted to produce oligomers for making polymers typically for binder applications, which have flame retardant property. The oligomers typically have repeated units disclosed herein of about 1 to 20 repeating units. The polymers typically have repeating units of about 1 to about 100,000, being most typically above 20 repeating units. It is believed that the binders can be formed at fast rates of reaction.

The polyols and/or oligomers of the present invention are capable of providing flame retardancy to the resulting binders without any other flame retardant element or material. In addition, the inclusion of these polyols and/or oligomers of the present invention provides dual or multi-benefits of being binders/crosslinkers, possible chain extenders, and imparting flame retardancy.

One type aqueous binder solution can be prepared by mixing one or more Polyols 1 to 5 directly with polyfunctional acids such as polyacrylamide (PAA). Another type binder solution can be obtained by pre-converting polyols to polyol-based oligomers by pre-reaction with diacids through an esterification reaction (described above). Binder compositions can be evaluated in a preliminary fashion by adding specific amounts to the surface of a hot plate heated to about 180° C. (or other temperature—please specify) at time zero in stroke/cure tests. Pools of binder mixtures can then be stroked back and forth in a regular fashion with a spatula, and the time needed to first attain a viable and self-supporting string can be recorded as well as the time at which the entire mass solidified into a tight mass.

For example, oligomers of any one or more of Polyols 1 to 5 can be condensed with polyacids such as PAA to prepare cured binder systems. Preparation of this type oligomer represents a type of procuring which might result in binder final stage curing times being decreased compared to the curing times involved when reacting polyols themselves with PAA. Also this type oligomer generally will have increased and adjustable viscosities compared to Polyols 1 to 5 that will aid in the binder properly wetting and adhering to fiberglass or other non-woven fibers during the initial stages of curing. Oligomer viscosities can be increased or decreased as needed by adjusting reaction times and temperatures as well as polyol/polyacid ratios. Another advantage of preparing this type of oligomer is that it increases the proportion of biobased and sustainable furan based polyols in the final binder composition and correspondingly reduces the amount of petrochemical-derived PAA in the final binder composition. Also since some of the hydroxyl groups of various polyols will already have been pre-reacted, less PAA will be needed, thus reducing the acidity and increasing the pH of starting binder composition.

In addition, sodium hypophosphite was typically added as a catalyst at fairly constant concentrations relative to the amount of dry solids incorporated in various binder compositions.

EXAMPLES

Descriptions of the experimental methods used to prepare Polyols 2, 4, and 5 and the use of Polyol 5 as a foam component are described below. These examples are provided to illustrate various embodiments of the invention and are not intended to limit the scope of the invention in any way.

Example 1

Method for Preparing Polyol 2

This example illustrates a process for making the 2-furoic triethanolamine ester (an example of Polyol 2).

Methyl 2-furoate (20.25 g) was placed in a round bottomed flask with triethanolamine (25.24 g) and cupric tetrafluoroborate (0.03 g). The mixture was heated to 179° C. over 4 hours and 50 minutes with stirring by magnetic stirbar using a short path distillation apparatus for methanol removal. The resulting oil was analyzed by 1H NMR spectroscopy and formation of the ester verified.

Example 2

Method for Preparing Polyol 4

This example illustrates a process for making the 2-furoic pentaerythritol ester (an example of Polyol 4).

2-Furoic acid (20.02 g) was placed in a round bottomed flask with pentaerythritol (24.40 g), 1-methyl-2-pyrrolidinone (9 mL), and tin (II) oxalate (0.05 g). The mixture was heated to 215° C. over 10 hours with stirring by a magnetic stirbar using a short path distillation apparatus for water removal. The resulting solid was analyzed by 1H NMR spectroscopy and formation of the ester verified.

Example 3

Method of Preparing Polyol 5

This example illustrates a process for making the 2-furoic tris(hydroxymethyl)aminomethane amide (an example of Polyol 5). This polyol was designated as Battelle Polyol 52958-64-29 for polyurethane foam application in Example 4.

Methyl 2-furoate (683.45 g) was placed in a round bottomed flask with tris(hydroxymethyl)aminomethane (690.21 g), methanol (400 mL), and sodium methoxide (25.11 g). The mixture was heated to 120° C. with stirring by magnetic stirbar using a short path distillation apparatus for methanol removal. The amide formation was followed by infrared spectroscopy. Once complete, the mixture was dissolved into tetrahydrofuran and catalyst and excess amine was removed by Amberlite® IR120 resin. The solvent was then removed by vacuum distillation. The resulting oil was analyzed by 1H NMR spectroscopy showing 98% purity.

Example 4

Rigid Polyurethane Foam Using Polyol 5 from Example 3

The objective was to determine flammability (Burning Rate) of rigid polyurethane (PU) foams prepared with Battelle Polyol 52958-64-29 (Polyol 5 produced from Example 3) in comparison to the reference foam prepared with conventional sucrose-based polyol, Jeffol SG-360. Jeffol SG-360 has a 4.2 functionality. The aromatic groups in the foams are mainly based on the amount of isocyanate content. Isocyanate index is the percentage of the calculated stoichiometric amount of isocyanate needed to react with all active hydrogen components in the formulation. Thus, an isocyanate index of 105 means that 105% of the amount of isocyanate stoichiometrically required to react with all active hydrogen compounds is used.

Water blown rigid PU foams were prepared at Isocyanate Index 105 with 25 wt % and 50 wt % Battelle Polyol 52958-64-29 in combination with 75% and 50% sucrose based polyol, respectively (Designations #2 and 4 in Table 2). The weight percentages of Battelle Polyol were based on the total amount of polyols in the polyol system. As such the 25 wt % and 50 wt % Battelle Polyols 52958-64-29 are referring to 8.3 wt % and 16.6 wt % Battelle Polyols 52958-64-29 based on the total weight of the foam.

The purpose of the experiment was to compare the flame retardancy of the foams with the same or similar densities and the same content of aromatic groups. The content of the aromatic groups in a foam is mainly presented by the amount of the isocyanate in the isocyanate system as shown by Isocyanate Index. In order to prepare foams with the same content of aromatic groups originating from the isocyanate, similar hydroxyl values from the polyol system of the foam are needed. As such, to match the hydroxyl values of the foams with Battelle Polyol 52958-64-29 (the Polyol 5 foam), the reference sucrose based foams were prepared with glycerol as a co-reactant so as to increase the hydroxyl values of the polyol system in the reference sucrose based foams. The hydroxyl value of Battelle Polyol 52958-64-29 reported by Battelle was 782 mg KOH/g, (Table 1).

Raw Materials

A list of raw materials used in this evaluation is shown in Table 1. All materials were used as received from suppliers.

Preparation and Testing of Foams

All foams were prepared using a standard laboratory high-torque mixer. The polyol component (the polyol system) and isocyanate component (the isocyanate system) were mixed for 10 seconds. Afterwards, the mixture was transferred into an open cake box before cream time. Foaming profile, including cream time, gel time, rise time, and tack-free time, was measured on all foams.

Foams for Burning Rate measurements were prepared using the same hand-mixing procedure by pouring foaming mixture into a paper box of 3"×18"×12¼" dimensions (Table 2).

In the case of foams prepared with Battelle Polyol 52958-64-29, this polyol was first melted at 80° C. and then mixed with Jeffol SG-360. 50%/50% and 75%/25% blends of Jeffol SG-360 and Battelle Polyol 52958-64-29 were stable for a couple of hours at room temperature. However, the blends separated into two phase systems after standing overnight.

After aging for a couple of days, the foams were cut and tested for density according to ASTM D 1622-03 and burning rate according to ASTM D 635-03 (Table 2). ASTM D 635-03 is a standard test method for rate of burning and/or extent and time of burning of plastics in a horizontal position.

Results:

In the case of foam formulations with Designation #1 and #2, the reaction profile was measured on samples with 50 grams of total polyols. In the case of foam formulations with Designation #3 and #4, the reaction profile was determined on samples with 100 grams of total polyols.

Foams were first prepared with 50% Battelle Polyol 52958-64-29 (foam formulation with Designation #2 in Table 2). The cream time of these foams was slower than that of the reference foams (Designation #1 in Table 2). After the cream time, the expansion of foams with 50% Battelle Polyol 52958-64-29 was very fast. In addition, these foams exhibited off-gassing (a sag) resulting in somewhat higher density in comparison to the reference foam (Designations #1 and #2 in Table 2, FIG. 1).

Foams were also prepared with 25% Battelle Polyol 52958-64-29 including a reference foam with the same aromatic content originating from the isocyanate (Designations #4 and #3 in Table 2, FIG. 2). For the foam with 25% Battelle Polyol 52958-64-29, the cream time was somewhat slower than in the case of the reference foam and the expansion of foam after the cream time was very fast. However, no off-gassing was observed, and foam based on 25% Battelle Polyol 52958-64-29 exhibited similar density as that of the reference foam (Designations #3 and #4 in Table 2).

The burning rate was measured on all foam formulations. In both sets of foams, foams with Battelle Polyol 52958-64-29 (Designations #2 and 4) exhibited lower burning rate. The burning rate of the foam with 25% Battelle Polyol 52958-64-29 was significantly lower than that of the reference foam (Designations #4 and #3 in Table 2). Visually, the charring rates of the two foams were comparable. These two foams had similar densities and apparent cell structure, and therefore the difference in burning rate can be ascribed to the presence of Battelle Polyol 52958-64-29.

The burning rate of the foam with 50% Battelle Polyol 52958-64-29 was slightly lower in comparison to the reference foam with the same concentration of aromatic groups from the isocyanate (Designations #2 and #1 in Table 2). However, these two foams had different densities. The apparent cell structure of these two foams was also different. It is well known that the cell structure can affect burning rate of the foam, which might explain much lower effect of the furan polyol on the burning rate in the foam with 50% Battelle Polyol 52958-64-29 (Designation #2) in comparison to that of the foam with 25% Battelle Polyol 52958-64-29 (Designation #4).

TABLE 1

| Materials | | |
|---|---|---|
| Designation | Type | Supplier |
| POLYOLS | | |
| Polyol 52958-64-29 2-furoic trisamide | Hydroxyl Value = 782; | BATTELLE |
| Jeffol SG-360 | Sucrose/glycerin-based polyol; Hydroxyl value = 361 (Eq. wt. = 155.4) | Huntsman |
| CROSSLINKERS | | |
| Superol V Glycerin | 1,2,3-Propanetriol; (Eq. wt = 30.67) | Procter & Gamble Chemicals |
| SURFACTANTS | | |
| Dabco DC193 | Polysiloxane | Air Products |
| CATALYSTS | | |
| Dabco 33LV | 33% Triethylene diamine in dipropylene glycol | TPI Momentive |
| ISOCYANATES | | |
| Rubinate M | Polymeric MDI; Eq. wt = 135.5 | Huntsman |

TABLE 2

Formulation screening of PU foams based on Battelle Polyols

| | | | Designation | | |
|---|---|---|---|---|---|
| | | 1 | 2 | 3 | 4 |
| | | | Sample designation | | |
| | F | Eqv. Weight | R-1 | B-1 | R-A-1 | B-2 |
| Polyol system | | | | | | |
| Jeffol SG-360 | | 155.4 | 85.6 | 50 | 92.82 | 75 |
| Polyol 52958-64-29 | | 71.4 | 0 | 50 | 0 | 25 |
| Superol V Glycerin | | 30.67 | 14.4 | 0 | 7.18 | 0 |
| Water | 2 | 9 | 4.5 | 4.5 | 4.5 | 4.5 |
| Dabco DC193 | | | 2 | 2 | 2 | 2 |
| Dabco 33LV | | | 1.8 | 1.8 | 1.8 | 1.8 |
| Niax A-1 | | | 0.1 | 0.1 | 0.1 | 0.1 |
| Isocyanate System | | | | | | |
| Rubinate M | | 135.5 | 219.1 | 218.93 | 192.25 | 192.24 |
| Isocyanate Index | | | 105 | 105 | 105 | 105 |
| % Battelle polyol on total polyols | | | 0 | 50 | 0 | 25 |
| Reaction Profile of Free-rise* | | | | | | |
| Mix time, sec. | | | 10 | 10 | 10 | 10 |
| Cream time, sec. | | | 30 | 49 | 22 | 25 |
| Gel time, sec. | | | 92 | 95 | 73 | 46 |
| Rise time, sec. | | | 117 | 125 | 105 | 62 |
| Tack-free time, sec. | | | 120 | 110 | 115 | 58 |
| Properties** | | | | | | |
| Free-rise density, pcf | | | 2.01 | 2.68 | 2.01 | 2.15 |
| Burn rate, mm/min | | | 332 ± 68 | 303 ± 46 | 379 ± 63 | 287 ± 29 |
| Comments | | | | | | |

*In the case of foam formulations with Designation #1 and #2, the reaction profile was measured on samples with 50 grams of total polyols. In the case of foam formulations with Designation #3 and #4, the reaction profile was determined on samples with 100 grams of total polyols.
**Foams for Burning rate testing were prepared with total of 100 grams of polyol using a paper box of 3" × 18" × 12¼" size.

CONCLUSION

2-Furoic tris(hydroxymethyl)aminomethane amide (a representative of Polyol 5), having a furan content of 48.1% weight, was used in a foam to verify it's suppression of flammability. Foams were developed having similar densities and the same aromatic content from isocyanate in order to directly correlate the flammability to changes in polyol. Battelle Polyol was used to replace 25% and 50% of the weight of the reference polyol mixture. 50 wt % loading of Battelle Polyol (B-1 or Designation #2) is not discussed in this section for its flame retardation properties because its foam was different from the reference foam (R-1 or Designation #1) in terms of densities and cell structures.

As seen in Tables 1-2, the reference foam (R-A-1) contained no Battelle Polyol and foam B-2 contained 25% weight replacement of the polyol fraction. Catalysts and isocyanate content were held constant and foam densities were very similar. In addition, the base polyol (also called "reference polyol") Jeffol SG-360 has a functionality of 4.2 to 5.0, glycerol has a functionality of 3, and Battelle Polyol 52958-64-29 has a functionality of 3. Therefore, the crosslinking capability of the reference or base polyol system is comparable or similar to that of the Battelle Polyol 52958-64-29. By keeping all other parameters the same or similar, any change to the burning rate (flame retardancy) of the foam can be contributed to the presence of Battelle Polyol.

According to results listed in tables, even a low furanic content of the Battelle Polyol (Designation #4 in Table 2), about 4% based on total foam weight, significantly decreased the flammability rate of the foam, and thus demonstrating the flame retardant effect of Polyol 5 of the present invention.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

The invention claimed is:

1. A flame retardant polyol comprising

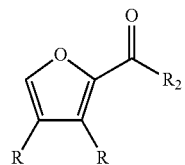

wherein each R is the same or different, and R can be hydrogen, ether, hydroxyl, or halogen, and $R_2$ represents one or more derivatives of glycerol, diglycerol, pentaerythritol, triethanolamine, diethanolamine, or tris(hydroxymethyl)aminomethane.

2. A flame retardant foam article obtained by incorporating one or more polyols, polyol mixtures, and/or oligomers of Polyol of claim 1.

3. The foam article of claim 2, wherein the total amount of polyols, polyol mixtures, and/or oligomers are present in the amount of about 0.25 wt % to about 78 wt % based on the total weight of the foam article.

4. A flame retardant binder obtained by incorporating one or more polyols, polyol mixtures, and/or oligomers of Polyol of claim 1.

5. An oligomer comprising a reaction product of a Polyol of claim 1, and a polyfunctional acid or a polyfunctional nitrile; or an oligomer that is the reaction product of mixtures of two or more polyols of Polyol of claim 1, and a polyfunctional acid or a polyfunctional nitrile; wherein the oligomer has one or more hydroxyl terminals.

* * * * *